US006187960B1

(12) United States Patent
Shaw

(10) Patent No.: US 6,187,960 B1
(45) Date of Patent: Feb. 13, 2001

(54) PROCESS FOR PRODUCING ORGANIC POLYSULFIDE COMPOUNDS

(75) Inventor: James E. Shaw, Bartlesville, OK (US)

(73) Assignee: Phillips Petroleum Company, Bartlesville, OK (US)

( * ) Notice: Under 35 U.S.C. 154(b), the term of this patent shall be extended for 0 days.

(21) Appl. No.: 08/388,541

(22) Filed: Feb. 14, 1995

(51) Int. Cl.$^7$ .................................................. C07C 323/00
(52) U.S. Cl. .................................................. 568/26; 568/21
(58) Field of Search ........................................ 568/21, 26

(56) References Cited

U.S. PATENT DOCUMENTS

| | | | |
|---|---|---|---|
| 2,695,316 | 11/1954 | McBride | 260/608 |
| 5,068,445 | * 11/1991 | Arrety | 568/21 |
| 5,155,275 | * 10/1992 | Shaw | 568/21 |
| 5,218,147 | * 6/1993 | Shaw | 568/21 |
| 5,232,623 | 8/1993 | Shaw | 252/183.13 |
| 5,283,368 | 2/1994 | Shaw | 568/45 |

* cited by examiner

Primary Examiner—James H. Reamer
(74) Attorney, Agent, or Firm—Richmond, Hitchcock, Fish & Dollar

(57) ABSTRACT

A process which can be used to produce organic polysulfide compounds is provided. The process comprises contacting, in the presence of a catalyst, an organic disulfide with sulfur under conditions sufficient to produce an organic polysulfide wherein the organic disulfide, sulfur, and catalyst are each present in an amount effective to produce an organic polysulfide and the catalyst comprises a base and a surfactant.

24 Claims, No Drawings

PROCESS FOR PRODUCING ORGANIC POLYSULFIDE COMPOUNDS

FIELD OF THE INVENTION

The present invention relates to a process for producing organic polysulfide compounds from organic disulfides.

BACKGROUND OF THE INVENTION

Organic polysulfides containing two to five or even more sulfur atoms in the molecules have been found useful for many purposes such as additives for elastomers, antioxidants for lubricating oils, intermediates for the production of organic chemicals, insecticides, germicides and as an additive to diesel fuels to improve the octane number and ignition qualities of these fuels. These compounds have also been found useful in the compounding of extreme pressure lubricants and in the acceleration of rubber treating processes.

Such polysulfide compounds can be prepared by reacting mercaptans with elemental sulfur in the presence of a basic catalyst. For example, Biensan et al (U.S. Pat. No. 3,308,166) discloses that polysulfides can be prepared from a mercaptan and sulfur catalyzed by an amine using an alcohol promoter.

It has been shown that an alkyl polysulfide can also be produced by direct addition of sulfur to an alkyl disulfide in the presence of alkali, ammonia, amine, or zinc oxide. For example, sulfur is taken up by a warm, stirred solution of ethyl disulfide containing 1% of triethylamine. See generally E. Reid, Organic Chemistry of Bivalent Sulfur, Vol. III, 1960.

However, it has been discovered that the addition of sulfur to an alkyl disulfide caused substantially incomplete reaction partly due to the low reactivity and solubility of sulfur in alkyl disulfide. Therefore, there is a need to develop an improved process for producing organic polysulfide compounds.

SUMMARY OF THE INVENTION

An object of the present invention is to provide a process for producing organic polysulfide compounds. Another object of the invention is to provide a process for producing organic polysulfide compounds under mild conditions. A further object of the present invention is to provide a process for producing polysulfide compounds at an increased reaction rate. Still another object of the invention is to produce an organic trisulfide compound. Yet still a further object of the present invention is to provide a process for producing an organic polysulfide from a mixture containing an organic disulfide. One of the advantages of the present invention is that an organic polysulfide can be produced in high yield at a mild condition. Other objects and advantages will become more apparent as the invention is more fully disclosed hereinbelow.

According to the present invention, a process which can be used to produce organic polysulfide compounds is provided. The process comprises contacting, in the presence of a catalyst, an organic disulfide with sulfur under conditions sufficient to produce the organic polysulfide. The organic disulfide, sulfur, and catalyst are each present in an amount effective to produce an organic polysulfide, and the catalyst comprises a basic catalyst and a surfactant.

DETAILED DESCRIPTION OF THE INVENTION

According to the first embodiment of the present invention, an organic polysulfide compounds having the formula of $R-S_n-R$, wherein each R can be the same or different and is each a hydrocarbyl radical having 1 to about 30, preferably about 1 to about 20, and most preferably 1 to 15 carbon atoms and n is a number greater than 2 but less than about 10, preferably in the range of from about 3 to about 8, more preferably from 3 to 5, and most preferably 3, can be produced by the process of the present invention. The hydrocarbyl radical can be linear or branched and can be alkyl, aryl, cycloalkyl, alkaryl, aralkyl, alkenyl radicals, or combinations of any two or more thereof. Preferably the hydrocarbyl radical is an alkyl radical.

According to the present invention, a process for producing an organic polysulfide is provided which comprises contacting an organic disulfide with elemental sulfur in the presence of a catalyst which comprises a basic catalyst and a surfactant. The basic catalyst can be any catalyst, which is not an alkylamine, that can catalyze the reaction of an organic disulfide and sulfur to form an organic polysulfide compound as defined hereinabove. The presently preferred catalyst comprises a basic catalyst which can be an inorganic base, an organic base, or combinations of any two or more thereof.

Suitable organic bases include, but are not limited to, tetramethylammonium hydroxide, tetraethylammonium hydroxide, tetrapropylammonium hydroxide, tetramethylammonium bisulfide, tetraethylammonium bisulfide, and combinations of any two or more thereof. Suitable inorganic bases include, but are not limited to, lithium hydroxide, sodium hydroxide, sodium hydrosulfide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R^1ONa$, $R^1OK$, $R^1SNa$ such as sodium methanethiolate, $R^1SK$, and combinations of any two or more thereof; where $R^1$ is a $C_1-C_{18}$ alkyl radical, or combinations of any two or more thereof. Among the bases, sodium hydroxide, sodium hydrosulfide, and sodium methanethiolate are preferred because they exert some synergistic effect with a surfactant and they are readily available and inexpensive.

The catalyst useful in the production of an organic polysulfide also comprises a surfactant. According to the present invention, any surfactant that facilitates the mixing of reactants into substantially a single phase can be used.

Generally, the surfactant comprises one or more compounds which exhibit surface-active properties. A preferred surfactant for use in the reaction system of the instant invention is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of any two or more thereof.

The presently preferred surfactant is an alkoxylated compound. Examples of suitable alkoxylated compounds include, but are not limited to, alkoxylated alcohols, alkoxylated mercaptans, sulfates of alkoxylated alcohols, alkoxylated phenols, sulfates of alkoxylated phenols, and combinations of any two or more thereof.

The alkoxylated alcohol useful in the present invention has a general formula of $R^2O[CH_2CH(R^3)O]_qH$ where $R^2$ is a $C_1-C_{20}$ hydrocarbyl radical selected from the group consisting of alkyl radical, alkylaryl radical, aryl radical, cycloalkyl radical, alkenyl radical, and combinations of any two or more thereof; Preferably $R^2$ is a $C_6-C_{18}$ alkyl radical. Most preferably $R^2$ is a $C_{10}-C_{16}$ alkyl radical; $R^3$ is selected from the group consisting of hydrogen, $C_1$–$C_{16}$ alkyl radicals, $C_2$–$C_{16}$ alkenyl radicals, and combinations of any two or more thereof; and q is a number of from 1 to about 20, preferably from about 2 to about 12, most preferably from 5 to 10. Generally $R^3$ can contain from 0 to about 16 carbon atoms. Preferably $R^3$ is a hydrogen or a $C_1$–$C_3$ alkyl radical. Most preferably $R^3$ is hydrogen. An example of suitable alkoxylated alcohol is TERGITOL 15-S-7 which is an ethoxylated alcohol, is manufactured and marketed by Union Carbide Corporation, and has the formula of $R^2O(CH_2CH_2O)_7H$ where $R^2$ is a secondary alkyl radical having 11–15 carbon atoms and 7 is the averaged number of the ethylene oxide units. Another example is an ethoxylated phenol having the same number of ethylene oxide units. Other suitable alkoxylated alcohols are also available from Union Carbide Corporation.

The sulfate of alkoxylated alcohol useful in the present invention has a general formula of $R^2O[CH_2CH(R^3)O]_qSO_3M$ where $R^2$ and $R^3$ are the same as those described above and M is an alkali metal or an alkaline earth metal or combinations of any two or more thereof. An example of suitable sulfate of alkoxylated alcohol is sodium sulfate of an ethoxylated alcohol having the formula of $R^2O(CH_2CH_2)_qSO_3$ Na in which $R^2$ and q are the same as those disclosed above.

Useful alkoxylated phenols and sulfates of alkoxylated phenols can have general formulas of $(R_3)_pArO[CH_2CH(R^3)O]_qH$ and $(R^2)_pArO[CH_2CH(R^3)]_qSO_3M$, respectively where $R^2$, $R^3$, and M are the same as those disclosed above, Ar is a phenyl group and p is an integer ranging from 0 to 5. Examples of these alkoxylated phenols are ethoxylated phenol $ArO(CH_2CH_2O)_qH$ and sodium sulfate of ethoxylated phenol $ArO(CH_2CH_2O)_qSO_3Na$ where Ar and q are the same as disclosed above.

The alkoxylated mercaptan useful in the present invention has a general formula of $R^2S[CH_2CH(R^3)O]_qH$ where $R^2$ and $R^3$ are the same as those described above. An example of an alkoxylated mercaptan is an ethoxylated mercaptan having the formula of $R^2S(CH_2CH_2O)_7H$ where $R^2$ is primarily a tertiary dodecyl group and 7 is the averaged number of ethylene oxide units. This ethoxylated mercaptan is a surfactant, commercially available from Phillips Petroleum Company, Bartlesville, Okla. under the trade name AQUA-CLEEN® II. Another example is an ethoxylated thiophenol having the same number of ethylene oxide units. Other suitable alkoxylated mercaptans are also available from Phillips Petroleum Company.

Quaternary ammonium salt useful in the present invention has the general formula $(R^4)_4N^+X^-$ where $R^4$ is an alkyl radical of from 1 to 20 carbon atoms; and X is selected from the group consisting of $Br^-$, $Cl^-$, $I^-$, $F^-$, $R^4CO_2^-$, $QSO_3^-$, $BF_4^-$, and $HSO_4^-$, where Q is an aryl, alkaryl or arylalkyl radical of 6 to 10 carbon atoms. It will be noted that a variety of anions are suitable as the component of the quaternary ammonium salts.

Useful quaternary ammonium salts according to the general formula given above include, but are not limited to, cetyltrimethylammonium bromide, hexadecyltrimethylammonium bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutyl ammonium fluoride, tetrabutylammonium tetrafluoroborate, and combinations of any two or more thereof.

An alkali metal alkyl sulfate of the general formula of $R^4OSO_3M$ can be used in the present invention, wherein $R^4$ and M are the same as those disclosed above. Examples of suitable compounds according to the general formula for the alkali metal alkyl sulfates include, but are not limited to, lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate, and combinations of any two or more thereof.

Useful alkali metal salts of alkanoic acids have the general formula of $R^4CO_2M$, where $R^4$ and M have the same meaning as given above. Examples of suitable alkali metal salts of alkanoic acids include, but are not limited to, lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and combinations of any two or more thereof.

Useful alkali metal salts of alkaryl sulfonic acids have the general formula of $(R^4)_pArSO_3M$ where $R^4$ and M are the same as those disclosed above, Ar is a phenyl group, and p is an integer ranging from 0 to 5.

Typical compounds within the group include, but are not limited to, sodium dodecylbenzenesulfonate, potassium dodecylbenzenesulfonate, lithium dodecylbenzenesulfonte, sodium tetradecylbenzenesulfonate, potassium hexadecylbenzenesulfonate, rubidium dodecylbenzenesulfonate, cesium dodecylbenzenesulfonate, sodium octadecylbenzenesulfonte, potassium octadecylbenzenesulfonate, sodium eicosylbenzenesulfonate, and combinations of any two or more thereof.

Examples of suitable 1-alkyl pyridinium salts include, but are not limited to, 1-dodecylpyridinium paratoluenesulfonate, 1-dodecylpyridinium chloride, 1-hexadecylpyridinium chloride, 1-hexadecylpyridinium paratoluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and combinations of any two or more thereof.

The weight ratio of a base to a surfactant can vary widely so long as the ratio can catalyze the reaction of organic disulfide and sulfur, preferably from about 1:1 to about 1:100, more preferably from about 1:5 to about 1:50, and most preferably 1:5 to 1:20, for best results. If a mixture of bases or surfactants is used, the weight ratio can be any ratio that catalyzes the reaction of organic disulfide sulfur and can be, for example, in the range of 1:1 to 999:1 for each base to other base or for each surfactant to other surfactant.

The catalyst used in the present invention, if containing a combination of bases and/or surfactants, can be made by properly mixing the components in the ratio described above and employing any suitable mixing means such as shaking or stirring. The preparation can also be done in-situ, i.e., mixing the components of the catalyst in a medium containing an organic disulfide and sulfur. Similar process for the preparation of such catalyst can be found in U.S. Pat. No. 5,232,623, disclosure of which is incorporated herein by reference. Furthermore, a base can also be prepared in-situ such as, for example, combining methyl mercaptan and sodium hydroxide or hydrogen sulfide and sodium hydroxide in a medium containing an organic disulfide and sulfur reactants to prepare sodium methanethioate or sodium hydrosulfide.

According to the present invention, an organic disulfide compound having the formula of R—S—S—R, wherein each R can be the same or different and are each a hydrocarbyl radical having 1 to about 30, preferably about 1 to about 20, and most preferably 1 to 15 carbon atoms can be used in the process of the present invention. The hydrocarbyl radical can be linear or branched and can be alkyl, aryl, cycloalkyl, alkaryl, aralkyl, alkenyl radicals, or combinations of any two or more thereof. Preferably the hydrocarbyl radical is an alkyl radical. The presently preferred organic disulfide compounds are dialkyl disulfides.

Examples of suitable organic disulfides include, but are not limited to, dimethyl disulfide, diethyl disulfide, diisopropyl disulfide, di-n-propyl disulfide, di-n-butyl disulfide, di-n-amyl disulfide, di-t-butyl disulfide, di-t-amyl disulfide, di-n-hexyl disulfide, dicyclohexyl disulfide, didecyl disulfide, didodecyl disulfide, di-t-dodceyl disulfide, diphenyl disulfide, dibenzyl disulfide, ditoluyl disulfide, and combinations of any two or more thereof. The presently most preferred organic disulfide is dimethyl disulfide.

The polysulfide can be prepared by the reaction of organic disulfides having the formula of R—S—S—R and elemental sulfur catalyzed by a catalyst disclosed above. The reaction is depicted as R—S—S—R+(n−2)S→$RS_nR$ where each R is the same as that described above and n is a number greater than 2 but less than 10, preferably from 3 to about 8, more preferably 3 to about 5, and most preferably 3. The reaction can be carried out in any suitable reaction vessel. The choice of reaction vessel is a matter of preference to those skilled in the art.

Conditions for contacting organic disulfides with elemental sulfur are any suitable conditions that can result in the production of an organic polysulfide compound and can include a temperature in the range of from about 20° C. to about 250° C., preferably from 50° C. to 150° C., for a time of from about 10 minutes to about 10 hours, preferably 30 minutes to 5 hours. The pressure can vary widely from about 1 atmosphere to about 30 atmospheres, preferably from about 1 atmosphere to about 3 atmospheres.

Generally, one of the reactants, either the organic disulfide or sulfur, is slowly added to the other reactant in the presence of the catalyst described above. The sulfur, upon addition, dissolves in the reaction medium containing the catalyst. Mixing of the solution and/or operating at higher than ambient temperatures will enhance the reaction rate. The amount of sulfur added depends on the desired sulfur content of the polysulfide product. For an average sulfur content of n sulfurs per polysulfide molecule, (n−2) moles of sulfur must be added per mole of organic disulfide. It is, however, preferred that about 0.5 to about 10, more preferably about 1 to about 5, and most preferably 1 to 3 moles of elemental sulfur per 1 mole of organic disulfide be used. The weight of the catalyst as a percentage of the weight of organic disulfide is a percentage that can catalyze the formation of an organic polysulfide and can be in the range of from 0.001 to 20%, preferably about 0.01 to 10%, and most preferably 0.05 to 5%.

The organic polysulfide compounds produced can be further processed such as purification, separation, recovery, or combinations of any two or more thereof by any methods known to one skilled in the art such as, for example, distillation. Thereafter, if necessary, the organic polysulfide product can be further deodorized and stabilized using any known methods such as, for example, those disclosed in the U.S. Pat. Nos. 5,206,439; and 5,218,147, disclosures of which are incorporated herein by reference.

The process of the invention can also be carried out continuously. For example, the contacting of organic disulfide with elemental sulfur in the process of the invention catalyst can be done by employing continuous stir tank reactors connected in series, packed columns or towers in which the invention catalyst is supported on a solid support, and other continuous flows that are readily within the realm of one skilled in the art.

The organic polysulfide compounds can be purified and/or recovered by any methods known to one skilled in the art such as distillation.

The following examples are provided to further illustrate the practice of the invention and are not intended to limit the scope of the invention of the claims.

EXAMPLE I

This example illustrates the process of the present invention employing a combination of sodium methanethiolate and an ethoxylated alcohol as catalyst for preparing dimethyl polysulfides.

To a 200 ml flask equipped with thermowell, magnetic stir bar, and condenser with $N_2$ inlet on top was added 0.20 g of 18.8% $CH_3SNa$ solution (aqueous), 0.60 g of Tergitol 15-S-7 (ethoxylated alcohol from Union Carbide), and 23.5 g of dimethyl disulfide. The mixture was heated to 50° C., and 16.0 g of elemental sulfur (powdered flowers of sulfur) was added in portions over 3–4 minutes. The sulfur dissolved immediately in the reaction mixture which became orange in color. The reaction mixture was stirred for 45 minutes at 50° C., and then cooled and filtered. The final dimethyl polysulfide product was a clear yellow liquid (40.0 g, 101% yield). GC analysis (20×⅛ in 2% OV-101 column, 50° C. initially, then 15° C./min, 150° C. injection port temperature, FID detector) showed that the product consisted of 21.3% dimethyl disulfide, 60.9% dimethyl trisulfide, 15.8% dimethyl tetrasulfide, and 2.0% dimethyl pentasulfide. These percentages are mole %. For weight %, the values are 16.0% disulfide, 61.1% trisulfide, 19.9% tetrasulfide, and 3.0% pentasulfide. Different product mixtures or pure components can be obtained by distillation.

EXAMPLE II

This example illustrates the invention process using a combination of sodium hydroxide and an ethoxylated alcohol to catalyze the reaction of dimethyl disulfide and sulfur.

The reaction was carried out the same way as in Example I except that 0.20 g of 50% aqueous NaOH replaced the $CH_3SNa$. GC analysis of the dimethyl polysulfide product showed that it consisted of 30.1% (mole %) of dimethyl disulfide, 56.5% trisulfide, 12.1% tetrasulfide, and 1.3% pentasulfide. Conversion of these values to weight % gave 23.4% disulfide, 58.8% trisulfide, 15.8% tetrasulfide, and 2.0% pentasulfide.

EXAMPLE III

This example shows the invention process employing a mixture of sodium hydrosulfide and an ethoxylated alcohol as catalyst for producing dimethyl polysulfides.

The reaction was carried out the same way as in Example I except the amounts of regents were as follows: 23.5 g of dimethyl disulfide, 0.15 g of 45% NaSH (aqueous), 0.5 g of Tergitol 15-S-7, and 24.0 g of element sulfur. GC analysis of the dimethyl polysulfide product showed that it consisted of 29.7% (mole %) of dimethyl disulfide, 53.5% trisulfide, 14.8% tetrasulfide, and 2.0% pentasulfide. Conversion of these values to weight % gave 22.8% disulfide, 55.0% trisulfide, 19.1% tetrasulfide, and 3.1% pentasulfide.

EXAMPLE IV

This example is a comparative example illustrating that without using a surfactant as catalyst component, the reaction of an organic disulfide and sulfur is very poor.

The reaction was carried out the same way as in Example I but no Tergitol 15-S-7 was included. The sulfur did not dissolve in the reaction mixture to any significant extent. GC analysis of the liquid phase showed that it consisted of 90.9% (mole %) dimethyl disulfide, 6.9% trisulfide, 1.9% tetrasulfide, and 0.3% pentasulfide.

EXAMPLE V

This is another comparative example illustrating that an alkylamine does not work well as catalyst component for producing organic polysulfides from organic disulfides.

The reaction was carried out the same way as in Example I except the CH$_3$SNa was replaced by 0.40 g of triethylamine. The sulfur did not dissolve in the reaction mixture. GC analysis of the liquid phase showed that it consisted of only dimethyl disulfide and a slight amount of triethylamine.

The results shown in the above examples clearly demonstrate that the present invention is well adapted to carry out the objects and attain the ends and advantages mentioned was well as those inherent therein. While modifications may be made by those skilled in the art, such modifications are encompassed within the spirit of the present invention as defined by the disclosure and the claims.

That which is claimed:

1. A process comprising contacting, in the presence of a catalyst, an organic disulfide with elemental sulfur under a condition sufficient to produce an organic polysulfide wherein said catalyst comprises a base which is not alkylamine and a surfactant; and said organic disulfide, sulfur, and catalyst are each present in an amount effective to produce an organic polysulfide.

2. A process according to claim 1 wherein said polysulfide has a formula of R—S$_n$—R wherein each R is a hydrocarbyl radical having 1 to about 30 carbon atoms per molecule of said polysulfide and n is a number greater than 2 and less than 10.

3. A process according to claim 2 wherein said hydrocarbyl radical has 1 to 15 carbon atoms per polysulfide molecule and n is a number from 3 to 5.

4. A process according to claim 1 wherein said organic polysulfide is dimethyl polysulfide.

5. A process according to claim 1 wherein said organic polysulfide is dimethyl trisulfide.

6. A process according to claim 1 wherein said base is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, sodium hydrosulfide, sodium bisulfide, potassium hydroxide, potassium hydrosulfide, potassium bisulfide, calcium hydroxide, magnesium hydroxide, sodium bicarbonate, sodium carbonate, sodium sulfide, sodium oxide, magnesium oxide, calcium oxide, calcium carbonate, sodium phenoxide, barium phenoxide, calcium phenoxide, R$^1$ONa, R$^1$SNa, R$^1$OK, R$^1$SK, and combinations of any two or more thereof; where R$^1$ is a C$_1$–C$_{18}$ alkyl radical, or combinations of any two or more thereof.

7. A process according to claim 1 wherein said base is sodium hydroxide.

8. A process according to claim 1 wherein said base is sodium hydrosulfide.

9. A process according to claim 8 wherein said sodium hydrosulfide is prepared in-situ by combining hydrogen sulfide and sodium hydroxide.

10. A process according to claim 1 wherein said base is sodium methanethiolate.

11. A process according to claim 10 wherein said sodium methanethiolate is prepared in-situ by combining methyl mercaptan and sodium hydroxide.

12. A process according to claim 1 wherein said surfactant is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of any two or more thereof.

13. A process according to claim 1 wherein said surfactant is an alkoxylated compound selected from alkoxylated mercaptans, alkoxylated alcohols, sulfates of alkoxylated alcohols, alkoxylated phenols, sulfates of alkoxylated phenols, and combinations of any two or more thereof.

14. A process according to claim 13 wherein said alkoxylated compound has the formula of R$^2$O(CH$_2$CH$_2$O)$_7$H wherein R$^2$ is a secondary alkyl radical having 11 to 15 carbon atoms and 7 is the averaged number of the ethylene oxide units.

15. A process for producing an organic polysulfide comprising contacting, in the presence of a catalyst, an organic disulfide with elemental sulfur wherein: said organic polysulfide has the formula of R—S$_n$—R; said catalyst comprises a base and a surfactant; said base is selected from the group consisting of inorganic bases and organic bases, and combinations of any two or more thereof; said surfactant is an alkoxylated compound selected from the group consisting of alkoxylated alcohols, alkoxylated mercaptans, and combinations of any two or more thereof; each R is a hydrocarbyl radical having 1 to about 30 carbon atoms; and n is a number greater than 2 and less than about 10.

16. A process according to claim 15 wherein: said base is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, sodium hydrosulfide, sodium bisulfide, potassium hydroxide, potassium hydrosulfide, potassium bisulfide, calcium hydroxide, magnesium hydroxide, sodium bicarbonate, sodium carbonate, sodium oxide, magnesium oxide, calcium oxide, calcium carbonate, sodium phenoxide, barium phenoxide, calcium phenoxide, R$^1$ONa, R$^1$SNa, R$^1$SK, R$^1$OK, and combinations of any two or more thereof; where R$^1$ is a C$_1$–C$_{18}$ alkyl radical, and combinations of any two or more thereof; said alkoxylated compound is an alkoxylated alcohol; each R is a hydrocarbyl radical having 1 to about 20 carbon atoms; and n is a number from about 3 to about 8.

17. A process according to claim 15 wherein said base is selected from the group consisting of sodium hydroxide, sodium hydrosulfide, sodium methanethiolate, and combinations of any two or more thereof; each R is a hydrocarbyl radical having 1 to 15 carbon atoms in each organic polysulfide molecule; said surfactant is an ethoxylated alcohol; and n is a number from 3 to 5.

18. A process according to claim 17 wherein said ethoxylated alcohol has a formula of $R^2O(CH_2CH_2O)_7H$ wherein $R^2$ is a secondary alkyl radical having 11 to 15 carbon atoms and 7 is the averaged number of the ethylene oxide units; and n is 3.

19. A process according to claim 18 wherein said base is sodium hydrosulfide.

20. A process according to claim 18 wherein said base is sodium methanethiolate.

21. A process according to claim 18 wherein said organic polysulfide is dimethyl trisulfide.

22. A process for producing dimethyl trisulfide comprising contacting dimethyl disulfide and elemental sulfide, in the presence of a catalyst comprising a base and an ethoxylated alcohol having a formula of $R^2O(CH_2CH_2O)_7H$, wherein said base is selected from the group consisting of sodium hydroxide, sodium hydrosulfide, sodium methanethiolate, and combinations of two or more thereof; and $R^2$ is a secondary alkyl radical having 11 to 15 carbon atoms and 7 is the averaged number of the ethylene oxide units.

23. A process according to claim 22 further comprising recovering said dimethyl trisulfide.

24. A process according to claim 1 wherein said polysulfide has a formula of $R-S_n-R$; said organic disulfide has a formula of $R-S-S-R$; each R is independently a hydrocarbyl radical having 1 to about 30 carbon atoms per molecule; n is a number greater than 2 and less than 10; said base is effective to catalyze the reaction of an organic disulfide and sulfur to form an organic polysulfide compound; said surfactant is effective to facilitate the mixing of reactants into substantially a single phase; the weight ratio of said base to said surfactant is in the range of from about 1:1 to about 1:100; the molar ratio of elemental sulfur to said organic disulfide is in the range of from about 0.5 to about 10; the weight percent of said catalyst as percentage of said organic disulfide is in the range of from about 0.001 to about 20%; and said process is carried out at a temperature in the range of from about 20° C. to about 250° C. and under a pressure in the range of from about 1 to about 30 atmospheres for about 10 minutes to about 10 hours.

* * * * *